(12) United States Patent
Kim

(10) Patent No.: US 10,835,582 B2
(45) Date of Patent: Nov. 17, 2020

(54) PEPTIDE FOR PREVENTING HEARING LOSS, AND COMPOSITION COMPRISING SAME

(71) Applicant: GemVax & KAEL CO., LTD., Daejeon (KR)

(72) Inventor: Sang Jae Kim, Seoul (KR)

(73) Assignee: GemVaX & KAEL CO. LTD., Daejeon (KR)

( * ) Notice: Subject to any disclaimer, the term of this patent is extended or adjusted under 35 U.S.C. 154(b) by 0 days.

(21) Appl. No.: 15/553,689

(22) PCT Filed: Feb. 18, 2016

(86) PCT No.: PCT/KR2016/001646
§ 371 (c)(1),
(2) Date: Aug. 25, 2017

(87) PCT Pub. No.: WO2016/137162
PCT Pub. Date: Sep. 1, 2016

(65) Prior Publication Data
US 2018/0036384 A1 Feb. 8, 2018

(30) Foreign Application Priority Data
Feb. 27, 2015 (KR) .................. 10-2015-0028410

(51) Int. Cl.
*A61K 38/45* (2006.01)
*A61K 38/17* (2006.01)
(Continued)

(52) U.S. Cl.
CPC .............. *A61K 38/45* (2013.01); *A23L 33/18* (2016.08); *A23L 33/40* (2016.08); *A61K 38/10* (2013.01);
(Continued)

(58) Field of Classification Search
CPC ........ A61K 38/45; A61K 38/17; A61K 38/10; A61P 27/16
See application file for complete search history.

(56) References Cited

U.S. PATENT DOCUMENTS

| 6,967,211 B2 | 11/2005 | Inoue |
| 7,030,211 B1 | 4/2006 | Gaudernack et al. |

(Continued)

FOREIGN PATENT DOCUMENTS

| CN | 1313773 A | 9/2001 |
| EP | 1020190 A3 | 10/2000 |

(Continued)

OTHER PUBLICATIONS

Greten et al. BMC Cancer, 2010, 10:209 (Year: 2010).*
(Continued)

*Primary Examiner* — Kimberly Ballard
*Assistant Examiner* — Stacey N MacFarlane
(74) *Attorney, Agent, or Firm* — Sterne, Kessler, Goldstein & Fox P.L.L.C.

(57) ABSTRACT

The present invention relates to a pharmaceutical composition for preventing and treating hearing loss. More particularly, the present invention relates to a composition including a telomerase-derived peptide, the composition being effective in the treatment and prevention of hearing loss due to an ototoxic drug. A peptide having a sequence of SEQ ID NO: 1, a peptide having 80% or more sequence homology to the sequence, or a fragment thereof, according to the present invention, has an excellent effect in the treatment and prevention of hearing loss due to an ototoxic drug.

17 Claims, 9 Drawing Sheets
Specification includes a Sequence Listing.

(51) Int. Cl.
*A61K 38/10* (2006.01)
*A61P 27/16* (2006.01)
*C07K 7/08* (2006.01)
*A23L 33/18* (2016.01)
*A23L 33/00* (2016.01)

(52) U.S. Cl.
CPC .............. *A61K 38/17* (2013.01); *C07K 7/08* (2013.01); *C12Y 207/07049* (2013.01); *A23V 2002/00* (2013.01); *A61P 27/16* (2018.01)

(56) References Cited

U.S. PATENT DOCUMENTS

| | | |
|---|---|---|
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 9,937,240 B2 | 4/2018 | Kim et al. |
| 10,039,811 B2 | 8/2018 | Kim et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2010/0003229 A1 | 1/2010 | Santos |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim et al. |
| 2015/0307859 A1 | 10/2015 | Kim |
| 2015/0343095 A1 | 12/2015 | Kim et al. |
| 2015/0353903 A1 | 12/2015 | Kim |
| 2016/0002613 A1 | 1/2016 | Kim et al. |
| 2016/0008438 A1 | 1/2016 | Kim et al. |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |
| 2018/0207241 A1 | 7/2018 | Kim |
| 2018/0318383 A1 | 11/2018 | Kim et al. |
| 2019/0030137 A1 | 1/2019 | Kim et al. |
| 2019/0032032 A1 | 1/2019 | Kim |
| 2019/0142894 A1 | 5/2019 | Kim et al. |

FOREIGN PATENT DOCUMENTS

| | | |
|---|---|---|
| EP | 1093381 B2 | 7/2009 |
| EP | 1817337 B1 | 1/2011 |
| JP | 2002520293 A | 7/2002 |
| JP | 2002522373 A | 7/2002 |
| JP | 2010252810 A | 11/2010 |
| JP | 2011515498 A | 5/2011 |
| JP | 2012500279 A | 1/2012 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20140104288 A | 8/2014 |
| WO | WO/2000/002581 * | 1/2000 |
| WO | WO-0007565 A2 | 2/2000 |
| WO | WO-2009025871 A1 | 2/2009 |
| WO | WO-2009120914 A1 | 10/2009 |
| WO | WO-2010003520 A2 | 1/2010 |
| WO | WO-2010012850 A1 | 2/2010 |
| WO | WO-2010022125 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO 2013/167298 A1 | 11/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO 2014/046983 A1 * | 3/2014 |
| WO | WO-2014046478 A1 | 3/2014 |
| WO | WO-2014046481 A1 | 3/2014 |
| WO | WO-2014046490 A1 | 3/2014 |
| WO | WO 2014/130909 A1 | 8/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

McGonigle, Biochem Pharmacology, 83:559-566, 2012 (Year: 2012).*
Weir et al., Cancers 2011, 3: 3114-3142 (Year: 2011).*

(56) References Cited

OTHER PUBLICATIONS

Francis and Cunningham, Frontiers in Cellular Neuroscience, vol. 11, Article 252, Aug. 2017.*
Staff et al., Telomerase (GV1001) vaccination together with gemcitabine in advanced pancreatic cancer patients, Int J Oncol. 45(3): 1293-303. Epub Jun. 11, 2014.*
Shaw et al., Current status of GV1001 and other telomerase vaccination strategies in the treatment of cancer. Expert Rev Vaccines. Sep. 2010; 9(9):1007-16.*
Rybak et al., Seminars in Hearing, 40(2):197-204, Epub Apr. 26, 2019; abstract only.*
Takada, Y et al. (2015). Ototoxicity-induced loss of hearing and inner hair cells is attenuated by HSP70 gene transfer. Mol. Ther. Methods Clin. Dev. 2:15019.*
Seoung-Ae Lee et al. (2013). Heat shock protein-mediated cell penetration and cytosolic delivery of macromolecules by a telomerase-derived peptide vaccine. Biomaterials 34:7495-7505.*
Altschul, S.F., et al., "Basic Local Alignment Search Tool," Journal of Molecular Biology 215(3):403-410, Elsevier, England (Oct. 1990).
Auerbach, R., et al., "Angiogenesis Assays: Problems and Pitfalls," Cancer Metastasis Reviews 19(1-2):167-172, Kluwer Academic, Netherlands (2000).
Beer, T.M., et al., "Phase II Study of Weekly Docetaxel in Symptomatic Androgen-independent Prostate Cancer," Annals of Oncology 12(9):1273-1279, Oxford University Press, England (2001).
Berendsen, H.J., "A Glimpse of the Holy Grail?," Science 282(5389):642-643, American Association for the Advancement of Science, United States (1998).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 9 pages.
Choi, S.G., "Recent Advances in Cancer Cachexia," Journal of Korean Oncology Nursing 11(1):20-25 (2011).
Co-pending U.S. Appl. No. 15/772,928, inventors Kim, S.J., et al., filed Nov. 3, 2016 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Dementia from Merck Manual, accessed on Jul. 29, 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood117(14):3720-3732, American Society of Hematology, United States (2011).
Du, C., et al., "Conformational and Topological Requirements of Cell-permeable Peptide Function," The Journal of Peptide Research 51(3):235-243, Munksgaard, Denmark (1998).
Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).
Eisenegger, C., et al., "The Role of Testosterone in Social Interaction," Trends in Cognitive Sciences 15(6):263-271, Elsevier Science, England (2011).
Engineer, D.R. and Garcia, J.M., "Leptin in Anorexia and Cachexia Syndrome," International Journal of Peptides 2012:Article ID 287457, Hindawi Publishing Corporation, United States (2012).
"Seoul National University Bundang Hospital excited because of '000'," Clinical trials of Dream Anticancer Drug without side effects with Kael & GemVax, 4 pages, Apr. 22, 2013.
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Fauce, S.R., et al., "Telomerase-Based Pharmacologic Enhancement of Antiviral function of Human CD8+ T Lymphocytes,"Immunology 181(10):7400-7406, American Association of Immunologists, United States (Nov. 2008).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fontanes, V., et al., "A cell permeable peptide inhibits Hepatitis C Virus Replication by Sequestering IRES Transacting Factors, " Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).

(56) References Cited

OTHER PUBLICATIONS

Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Guo, R.F., et al., "Regulatory Effects of Eotaxin on Acute Lung Inflammatory Injury," Journal of Immunology 166(8):5208-5218, American Association of Immunologists, United States (2001).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability and Written Opinion for International Application No. PCT/KR2015/014099, The International Bureau of WIPO, dated Jun. 27, 2017, 16 pages.
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/KR2014/012502, The International Bureau of WIPO, Geneva, Switzerland, dated Jun. 21, 2016, 22 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Application No. PCT/KR2014/010035, Korean Intellectual Property Office, Republic of Korea, dated Apr. 26, 2016, 13 pages.
International Preliminary Report on Patentability for International Patent Application No. PCT/KR2013/004156, The International Bureau of WIPO, Geneva, Switzerland, dated Nov. 11, 2014, 15 pages.
International Search Report and Written Opinion for International Application No. PCT/KR2016/012613, Korean Intellectual Property Office, Republic of Korea, dated Feb. 2, 2017, 14 pages
International Search Report for Application No. PCT/KR2016/007192, dated Sep. 12, 2016, 12 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2013/008459, Korean Intellectual Property Office, Republic of Korea, dated Dec. 23, 2013, 8 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
Jaattela, M., "Over-expression of Hsp70 Confers Tumorigenicity to Mouse Fibrosarcoma Cells," International Journal of Cancer 60(5):689-693, Wiley-Liss, United States (1995).

(56) References Cited

OTHER PUBLICATIONS

Jain, R.K., "Barriers to Drug Delivery in Solid Tumors," Scientific American 271(1):58-65, Scientific American, Inc., United States (Jul. 1994).
Jemal, A., et al., "Cancer Statistics, 2008," CA: A Cancer Journal for Clinicians 58(2):71-96, Wiley, United States (2008).
Kalnins, A., et al., "Sequence of the Lacz Gene of *Escherichia coli*," The EMBO Journal 2(4):593-597, Wiley Blackwell, England (1983).
Kern, K.A. and Norton, J.A., "Cancer Cachexia," Journal of Parenteral and Enteral Nutrition 12(3):286-298, Sage Publications, United States (1988).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H., et al., "Inhibition of HIV-1 Reactivation by a Telomerase-Derived Peptide in a HSP90-Dependent Manner,"Scientific Reports 6: 28896, Nature Publishing Group, England (Jul. 2016).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).
Kocsis, J., et al., "Serum Level of Soluble 70-kD Heat Shock Protein is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Kyte, J.A., et al., "Telomerase Peptide Vaccination Combined with Temozolomide: A Clinical Trial in Stage IV Melanoma Patients," Clinical Cancer Research 17(13):4568-4580,American Association of Cancer Research, United States (2011).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "A Telomerase-Derived Peptide Regulates Reactive Oxygen Species and Hepatitis C Virus RNA Replication in HCV-Infected Cells Via Heat Shock Protein 90,"Biochemical and Biophysical Research Communications 471(1):156-162, Elsevier, United States (Feb. 2016).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).

Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Mandal, A., "Types of Fibrosis," Retrieved from the internet on Jul. 3, 2014, pp. 1-3.
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Massague, J., "Tgf-Beta Signal Transduction," Annual Review of Biochemistry 67:753-791, Annual Reviews, United States (1998).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (2014).
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL:http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: the Evolving World of Hsp70," Annals of the New York Academy of Sciences 1113:1-14, Blackwell, United States (2007).
Morishita, M., and Peppas, N.A., "Is the Oral Route Possible for Peptide and Protein Drug Delivery?," Drug Discovery Today 11(19-20):905-910, Elsevier Science Ltd., England (2006).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).

(56) References Cited

OTHER PUBLICATIONS

Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
National Horizon Scanning Centre News on Emerging Technologies in Healthcare, GV1001 for Advanced and/or Metastatic Pancreatic Cancer, Published Apr. 2008.
Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Scientific Publishers, Ireland (2010).
NCBI, Reference Sequence: XP_003776612.1 (Jul. 17, 2012).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences USA 98(18): 10308-10313, National Academy of Sciences, United States (2001).
Olney, J.W., et al., "Pathological Changes Induced in Cerebrocortical Neurons by Phencyclidine and Related Drugs," Science 244(4910):1360-1362, American Association for the Advancement of Science, United States (Jun. 1989).
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Albini, A., et al., "Cancer Prevention by Targeting Angiogenesis," Nature reviews Clinical oncology 9(9):498-509, Nature Pub Group (2012).
Pearson, W.R. and Lipman, D.J., "Improved Tools for Biological Sequence Comparison," Proceedings of the National Academy of Sciences of the United States of America 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Extended European Search Report for Application No. EP14808179, dated May 24, 2017, 24 pages.
Pfosser, A., et al., "Liposomal HSP90 Cdna Induces Neovascularization via Nitric Oxide in Chronic Ischemia," Cardiovascular Research 65(3):728-736, Oxford Journals, England (2005).
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1): 2 pages, May 24, 2015.
Supplemental European Search Report for Application No. EP14808179, dated Jan. 10, 2017, 13 pages. 4099.
Varma, N., et al., "Role of hTERT and WT1 Gene Expression in Disease Progression and Imatinib Responsiveness of Patients with BCR-ABL Positive Chronic Myeloid Leukemia," Leukemia and Lymphoma 52(4):687-693, Informa Healthcare, London (Apr. 2011).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Rosenbloom, J., et al., "Strategies for Anti-fibrotic Therapies," Biochimica et Biophysica Acta 1832(7):1088-1103, Elsevier Pub. Co., Netherlands (2013).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
Roubenoff, R., et al., "Adjuvant Arthritis as a Model of Inflammatory Cachexia," Arthritis and Rheumatism 40(3):534-539, Wiley-Blackwell, United States (1997).
Rudinger, J., "Characteristics of the Amino Acids as Components of a Peptide Hormone Sequence," in Peptide Hormones, Parsons, J.A., ed., University Park Press, United States (1976).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Schwarze, S.R., et al., "In Vivo Protein Transduction: Delivery of a Biologically Active Protein Into the Mouse," Science 285(5433):1569-1572, American Association for the Advancement of Science, United States (1999).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Shay, J.W., and Wright, W.E., "Telomerase Therapeutics for Cancer: Challenges and New Directions," Nature Reviews. Drug Discovery 5(7):577-584, Nature Publishing Group, England (2006).
SIGMA Genosys, "Designing Custom Peptides," accessed at http://www.sigma-genosys.com/peptide_design.asp, Accessed on Dec. 16, 2004, 2 pages.
Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).
Smith, T.F. and Waterman, M.S., "Comparison of Biosequences," Advances in Applied Mathematics 2(4):482-489, Academic Press, Inc., United States (Dec. 1981).
Song, J., et al., "Characterization and Fate of Telomerase-Expressing Epithelia during Kidney Repair," Journal of the American Society of Nephrology 22(12):2256-2265, American Society of Nephrology, United States (2011).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
ClinicalTrials.gov, "Adjuvant Leuprolide with or without Docetaxel in High Risk Prostate Cancer After Radial Prostatectomy," Identifier

(56) References Cited

OTHER PUBLICATIONS

NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.
National Center for Biotechnology Information, "Hormones," MeSH Database, Bethesda, accessed at http://www.ncbi.nlm.nih.gov/mesh/68006728, accessed on May 8, 2017, 3 pages.
National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-enlargement-benign-prostatic-hyperplasia, accessed Sep. 2014, 14 pages.
International Preliminary Report on Patentability and Written Opinion for International Application No. PCT/KR2016/001646, Korean Intellectual Property Office, Republic of Korea, dated May 20, 2016, 13 pages.
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Rowe-Rendleman, C. and Glickman, R.D., "Possible therapy for age-related macular degeneration using human telomerase," Brain Research Bulletin 62(6):549-553, Elsevier Science Inc., United States (2004).
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).
Tisdale, M.J., "Catabolic Mediators of Cancer Cachexia," Current Opinion in Supportive and Palliative Care, 2(4):256-261, Lippincott Williams & Wilkins, United States (2008).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).

Voet, D. and Voet, J.G., "Abnormal Hemoglobins," in Biochemistry, 2nd Edition, Chapter 9, pp. 235-241, John Wiley & Sons, Inc., United States (1995).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
Written Opinion for International Application No. PCT/KR2014/003425, Korean Intellectual Property Office, Republic of Korea, dated Jul. 21, 2014, 13 pages
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2013/008459, Korean Intellectual Property Office, Republic of Korea, dated Dec. 23, 2013, 9 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Written Opinion for International Patent Application No. PCT/KR2013/004156, Korean Intellectual Property Office, Republic of Korea, dated Aug. 14, 2013, 13 pages.
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).

(56) References Cited

OTHER PUBLICATIONS

Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).

Yeh, C.H., et al., "Clinical Correlation of Circulating Heat Shock Protein 70 in Acute Leukemia," Leukemia Research 34(5):605-609, Pergamon Press, England (2010).

Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).

Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).

Zhou, J., et al., "PI3K/Akt is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).

Petrylak D.P., "The Treatment of Hormone-Refractory Prostate Cancer: Docetaxel and Beyond," Reviews in Urology 8 (Suppl 2): S48-S55, United States (2006).

Shay, J.W., and Keith, W.N., "Targeting Telomerase for Cancer Therapeutics," in: British Journal of Cancer 98(4):677-683, Nature Publishing Group on behalf of Cancer Research UK (2008).

Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).

Ross, C.J.D., et al., "Genetic Variants in TPMT and CMOT are associated with hearing loss in children receiving cisplatin chemotherapy," Nature Genetics 41(12):1345-1350, Nature Publishing Group, United States (2009).

Tarantino, G., et al. "Spleen: a New Role for an Old Player?," World Journal of Gastroenterology, 17(33):3776-3784, Baishideng Publishing Group, United States (Sep. 2011).

Godet, Y., et al., "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response," *Clinical Cancer Research* 18(10):29432953, American Association for Cancer Research Inc., United States (2012).

* cited by examiner

COCHLEA　　　　　　　　　AMPULLA

COCHLEA　　　　　　　　　AMPULLA

COCHLEA          AMPULLA

PEP1 0.1mg/kg          PEP1 1mg/kg

PEP1 10mg/kg           PEP1 100mg/kg

SEQUENCE LISTING

<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
```

-continued

```
            370                 375                 380
Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800
```

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
            850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
            930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
            1010                1015                1020

Gln Val Trp Lys Asn Pro Thr Phe Phe Leu Arg Val Ile Ser Asp
            1025                1030                1035

Thr Ala Ser Leu Cys Tyr Ser Ile Leu Lys Ala Lys Asn Ala Gly
            1040                1045                1050

Met Ser Leu Gly Ala Lys Gly Ala Ala Gly Pro Leu Pro Ser Glu
            1055                1060                1065

Ala Val Gln Trp Leu Cys His Gln Ala Phe Leu Leu Lys Leu Thr
            1070                1075                1080

Arg His Arg Val Thr Tyr Val Pro Leu Leu Gly Ser Leu Arg Thr
            1085                1090                1095

Ala Gln Thr Gln Leu Ser Arg Lys Leu Pro Gly Thr Thr Leu Thr
            1100                1105                1110

Ala Leu Glu Ala Ala Ala Asn Pro Ala Leu Pro Ser Asp Phe Lys
            1115                1120                1125

Thr Ile Leu Asp
    1130

<210> SEQ ID NO 3
<211> LENGTH: 16
<212> TYPE: PRT
<213> ORGANISM: Artificial Sequence
<220> FEATURE:
<223> OTHER INFORMATION: Modified SEQ ID 1
<220> FEATURE:
<221> NAME/KEY: MISC_FEATURE
<222> LOCATION: (1)..(1)
<223> OTHER INFORMATION: NH2-Glu(OtBu)
<220> FEATURE:

```
<221> NAME/KEY: MISC_FEATURE
<222> LOCATION: (3)..(3)
<223> OTHER INFORMATION: Arg(Pbf)
<220> FEATURE:
<221> NAME/KEY: MISC_FEATURE
<222> LOCATION: (8)..(8)
<223> OTHER INFORMATION: Thr(tBu)
<220> FEATURE:
<221> NAME/KEY: MISC_FEATURE
<222> LOCATION: (9)..(9)
<223> OTHER INFORMATION: Ser(tBu)
<220> FEATURE:
<221> NAME/KEY: MISC_FEATURE
<222> LOCATION: (10)..(11)
<223> OTHER INFORMATION: Arg(Pbf)Leu
<220> FEATURE:
<221> NAME/KEY: MISC_FEATURE
<222> LOCATION: (12)..(12)
<223> OTHER INFORMATION: Arg(Pbf)
<220> FEATURE:
<221> NAME/KEY: MISC_FEATURE
<222> LOCATION: (16)..(16)
<223> OTHER INFORMATION: Lys(Boc)-2-chloro-Trityl Resin

<400> SEQUENCE: 3

Glu Ala Arg Pro Ala Leu Leu Thr Ser Arg Leu Arg Phe Ile Pro Lys
1               5                   10                  15
```

PEPTIDE FOR PREVENTING HEARING LOSS, AND COMPOSITION COMPRISING SAME

CROSS-REFERENCE TO RELATED APPLICATIONS

This application is the U.S. national phase of PCT/KR2016/001646, filed Feb. 18, 2016, which claims foreign priority to KR 10-2015-0028410, filed Feb. 27, 2015, which are hereby incorporated by reference herein in its entirety.

REFERENCE TO SEQUENCE LISTING SUBMITTED ELECTRONICALLY VIA EFS-WEB

The content of the electronically submitted sequence listing (Name: 2473_0990001_SeqListing.TXT; 11,038 bytes; and Date of Creation: Aug. 23, 2017) was originally submitted in the International Application No. PCT/KR2016/001646 and is incorporated herein by reference in its entirety.

BACKGROUND OF THE INVENTION

Field of the Invention

The present invention relates to a peptide having an effect of preventing hearing damage and a pharmaceutical composition including the same, and more particularly, to a telomerase-derived peptide having an effect of preventing hearing damage due to an ototoxic drug and a pharmaceutical composition for preventing hearing damage which includes the peptide.

Background Art

The anatomy of an ear is divided into the outer ear, the middle ear, and the inner ear, and the inner ear consists of the cochlea responsible for hearing, vestibule and semicircular canals that are responsible for a sense of equilibrium, and the vestibulocochlear nerve connected thereto.

Hearing damage results from damage to one of the outer ear, the middle ear, and the inner ear or multiple parts thereof. There are four types of hearing damage. The first most common type is sensorineural hearing loss that occurs as a result of loss of or damage to auditory cells (hair cells) in the cochlea constituting the inner ear. The second type is conductive hearing loss that occurs when there is a problem with the outer ear or the middle ear, resulting in sound not being conducted adequately to the inner ear. The third type is mixed hearing loss that occurs when sensorineural and conductive hearing losses are both present. The fourth type is auditory neuropathy that occurs when there is a problem with the auditory nerve transmitting a sound signal to the brain.

The term ototoxicity refers to a symptom of the inner ear due to a therapeutic agent or a chemical, i.e., dysfunction of the pheripheral organ and nervous tissue responsible for hearing and vestibular function and a degenerative change in tissue cells.

Aminoglycoside antibiotics and platinum-based anticancer drugs exhibit fetal nephrotoxicity and ototoxicity by repeated administration, and, in most cases, nephrotoxicity is often reversible, but ototoxicity is permanent. Due to these toxicities, highly effective drugs cannot be prescribed primarily unless drug administration effects are significant enough to withstand the side effects of aminoglycoside antibiotics and platinum-based anticancer drugs. The mechanism of apoptosis by ototoxic drugs has gradually become discovered, and attempts to prevent hearing loss by protecting hair cells using a method such as neutralization of reactive oxygen species (ROS), suppression of apoptosis-inducing enzymes, anti-inflammation, treatment with a neurotropic substance, and the like, and research thereon have been conducted. However, due to difficulties in the toxicity of a drug itself and a method of delivering the drug to the inner ear, clinical application thereof is insignificant. Ototoxicity due to an aminoglycoside antibiotic progresses while the drug is absorbed into the inner ear and accumulated in hair cells of the inner ear.

Furosemide is a type of diuretic that promotes diuretic action and is used in patients with congestive heart failure, renal edema, hepatic edema, hypertension, and the like. It has been reported that furosemide exhibits a strong diuretic action and is used even for pre-eclampsia, ascites, and peripheral vascular edema, but when administered in a large amount or for a long period of time, the drug causes electrolyte imbalance and acute hypotension. In addition, furosemide has been reported to cause auditory disorders, tinnitus, or hearing loss.

In addition, several risk factors capable of causing ototoxicity are known. Generally, it is known that, as a dose of an ototoxic drug increases and a period of use of the drug increases, the possibility of ototoxicity becomes high, but the degree of ototoxicity is affected by ages of patients (in particular, 65 years or older), an ototoxic drug administered in combination, previous ototoxic drug use, previous exposure to noise, existing hearing and balance disorders, kidney dysfunction, liver function, pyrexia, hypovolemia, bacteremia, and the like.

SUMMARY OF THE INVENTION

Technical Problem

Therefore, in the present study, the efficacy and safety of a telomerase-derived peptide were evaluated in an ototoxicity-inducing animal model. Through experiments, an effect of the telomerase-derived peptide on preventing hearing loss and damage to the inner ear due to ototoxicity was verified, and this indicates that the damage to the inner ear is caused by stresses such as an ototoxic drug, noise, and hypoxia and a final mechanism of damage to hair cells is apoptosis by ROS, and thus the telomerase-derived peptide may protect the inner ear from being damaged and also have an effect of recovering from damaged inner ears. Accordingly, since the present invention may be applied to recovery and treatment of damaged inner ears, it may be expected to be a great help to hearing loss treatment without side effects.

Technical Solution

To achieve the objective of the present invention, one aspect of the present invention may provide a composition for treating and preventing hearing loss, the composition including a peptide comprising an amino acid sequence of SEQ ID NO: 1, a peptide having 80% or more sequence homology to the amino acid sequence, or a fragment thereof.

In the composition according to one aspect of the present invention, the fragment may be a fragment consisting of three or more amino acids.

In the composition according to one aspect of the present invention, the hearing loss may be caused by administration of an ototoxic drug or ototoxic drug treatment.

In the composition according to one aspect of the present invention, the ototoxic drug may include one or more drugs selected from the group consisting of salicylates, nonsteroidal anti-inflammatory drugs, antibiotics, diuretics, chemotherapeutic agents, quinines, mucosal protective drugs, and anticancer drugs.

In the composition according to one aspect of the present invention, the antibiotics may be aminoglycoside-based antibiotics, and the anticancer drugs may be platinum-based anticancer drugs.

In the composition according to one aspect of the present invention, the aminoglycoside-based antibiotics may include kanamycin, and the platinum-based anticancer drugs may include cisplatin or carboplatin.

In the composition according to one aspect of the present invention, the diuretics may include furosemide.

In the composition according to another aspect of the present invention, the hearing loss may include hearing loss and tinnitus according to degenerative changes in a pheripheral organ and nervous tissue of the inner ear.

According to still another aspect of the present invention, the composition may be a pharmaceutical composition.

According to yet another aspect of the present invention, the composition may be a food composition.

According to yet another aspect of the present invention, there is provided a method of treating and preventing hearing loss, the method including administering the composition described above to a subject.

According to yet another aspect of the present invention, there is provided a kit for treating and preventing hearing loss, the kit including: the composition described above; and a manual.

In the kit according to yet another aspect of the present invention, the manual may include content on administering the composition described above.

According to yet another aspect of the present invention, there is provided a use of a peptide in terms of hearing loss to prepare the composition described above, the peptide including a peptide having an amino acid sequence of SEQ ID NO: 1, a peptide having 80% or more sequence homology to the amino acid sequence, or a fragment thereof.

Advantageous Effects

According to the present invention, a composition capable of effectively protecting against hearing loss can be provided. Thus, the composition according to the present invention can be applied to the treatment and prevention of hearing loss, and, in particular, can be used to treat hearing loss due to an ototoxic drug.

In addition, a peptide according to the present invention, which is a peptide having a sequence of SEQ ID NO: 1 (PEP1), a peptide having a sequence with 80% homology to the above-described sequence, or a fragment thereof, has an effect of treating and preventing hearing loss.

DETAILED DESCRIPTION OF THE DRAWINGS/FIGURES

Figure 11:
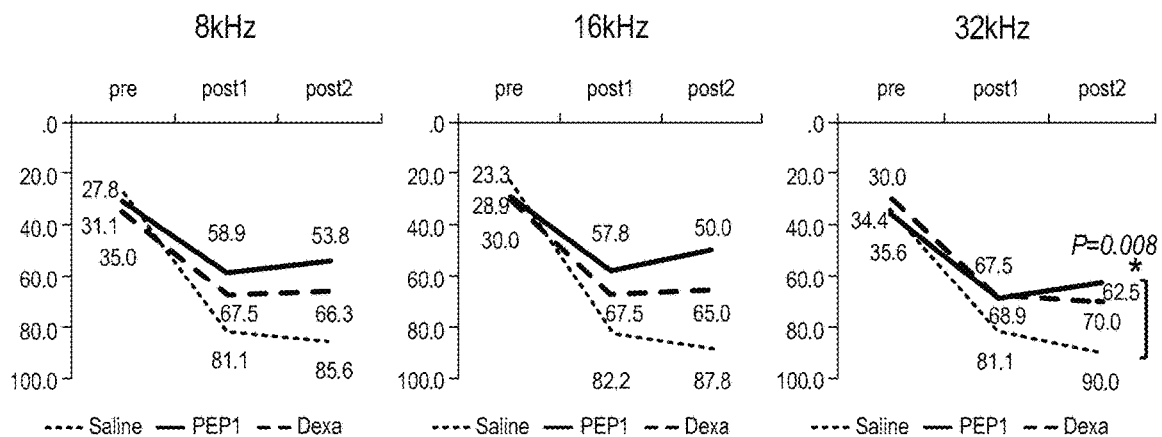

FIG. 11 illustrates graphs showing measurement values of frequency-dependent hearing changes through an ABR test of ototoxic animal models including PEP1-administered Experimental Group 1, dexamethasone-administered Experimental Group 2, and saline solution-administered Control 1, according to the schedule of Experiment D1, i.e., prior to the administration of an ototoxic drug, on day 7 after the drug administration, and on day 14 after the drug administration.

Figure 12:
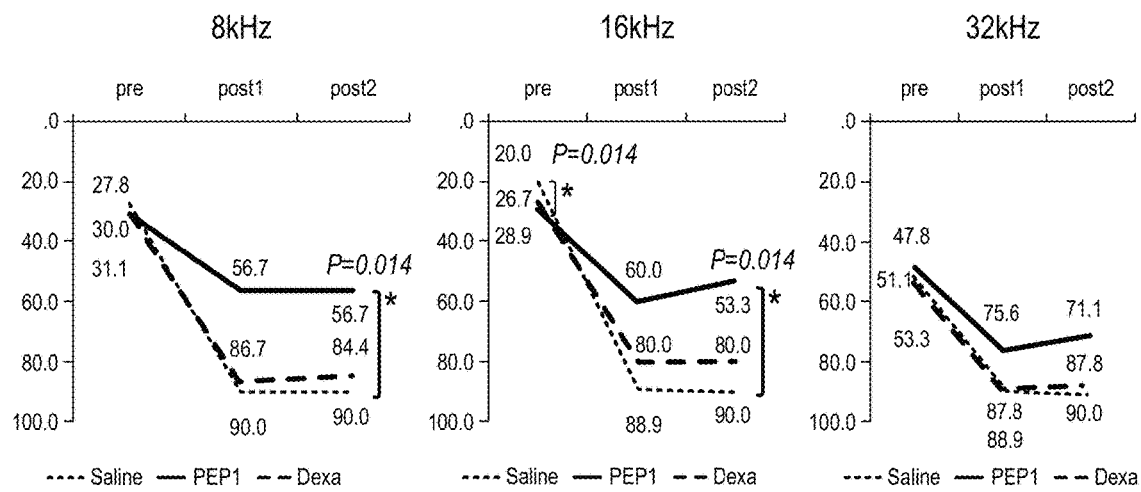

FIG. 12 illustrates graphs showing measurement values of frequency-dependent hearing changes through an ABR test of ototoxic animal models including PEP1-administered Experimental Group 3, dexamethasone-administered Experimental Group 4, and saline solution-administered Control 2, according to the schedule of Experiment D3, i.e., prior to the administration of an ototoxic drug, on day 7 after the drug administration, and on day 14 after the drug administration.

Figure 13:
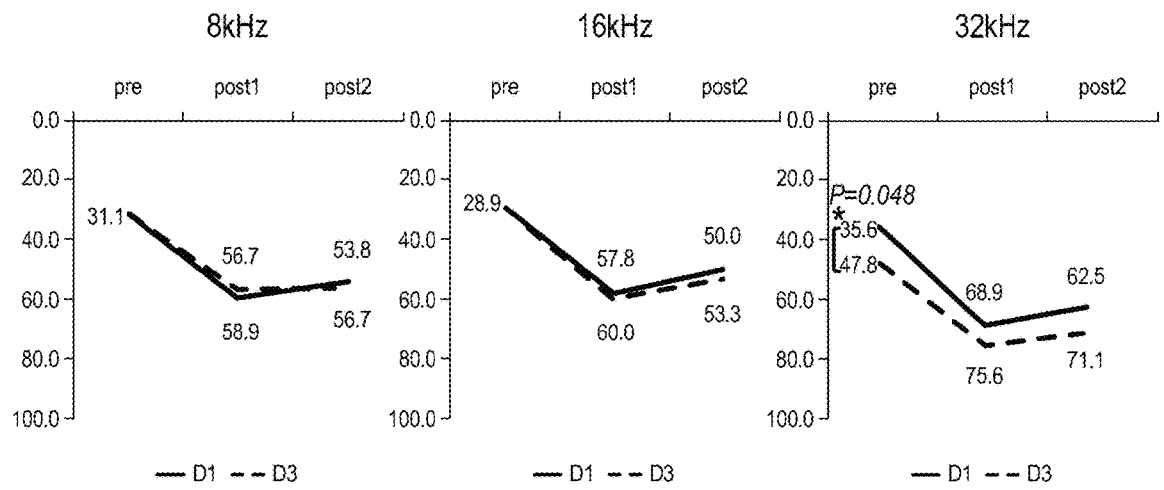

FIG. 13 illustrates graphs comparatively showing ABR test measurement values of frequency-dependent hearing changes of PEP1-administered Experimental Groups 1 and 3 as ototoxic animal models according to the schedules of Experiments D1 and D3, respectively, i.e., prior to the administration of an ototoxic drug, on day 7 after the drug administration, and on day 14 after the drug administration.

Figure 14:
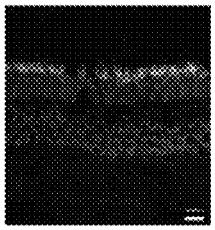

FIG. 14 illustrates confocal scanning microscope images acquired by observing the viability of hair cells at basal, mid, and apex of the cochlea after performing biopsy on ototoxic animal models including PEP1-administered Experimental Group 1, dexamethasone-administered Experimental Group 2, and saline solution-administered Control 1, respectively, according to the schedule of Experiment D1.

Figure 15:
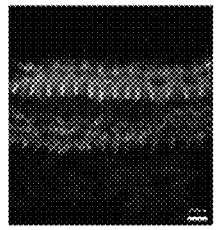

FIG. 15 illustrates confocal scanning microscope images acquired by observing the viability of hair cells at basal, mid, and apex of the cochlea after performing biopsy on ototoxic animal models including PEP1-administered Experimental Group 3, dexamethasone-administered Experimental Group 4, and saline solution-administered Control 2, respectively, according to the schedule of Experiment D3.

Figure 16:
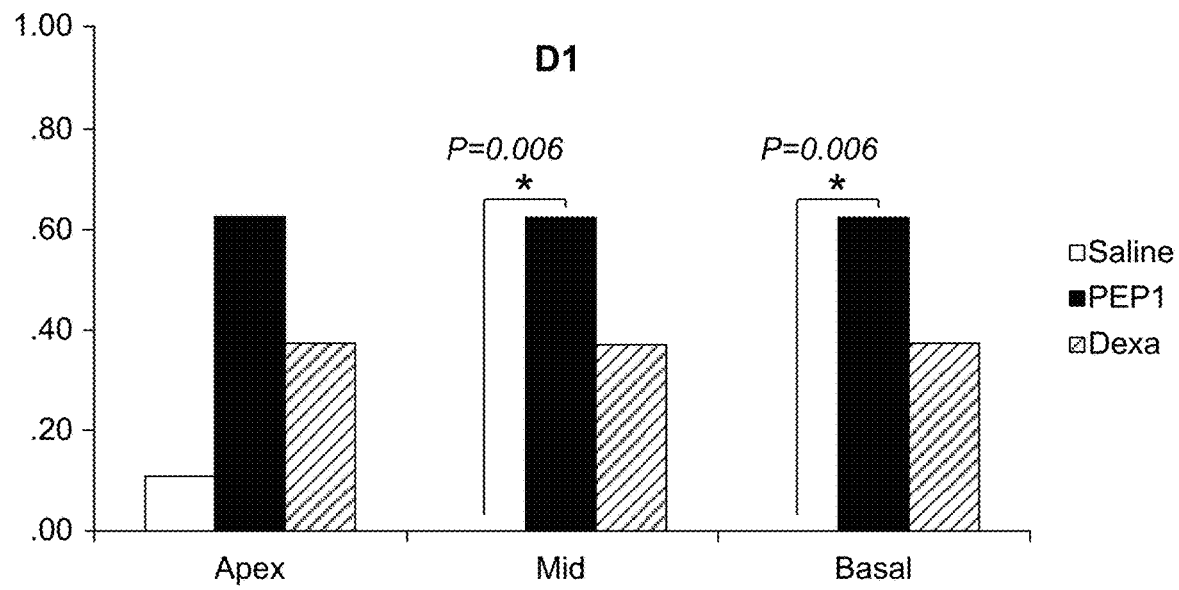

FIG. 16 is a graph showing quantitative analysis results of a ratio of normal hair cells of basal, mid, and apex of the cochlea after performing biopsy on ototoxic animal models including PEP1-administered Experimental Group 1, dexamethasone-administered Experimental Group 2, and saline solution-administered Control 1, respectively, according to the schedule of Experiment D1.

Figure 17:
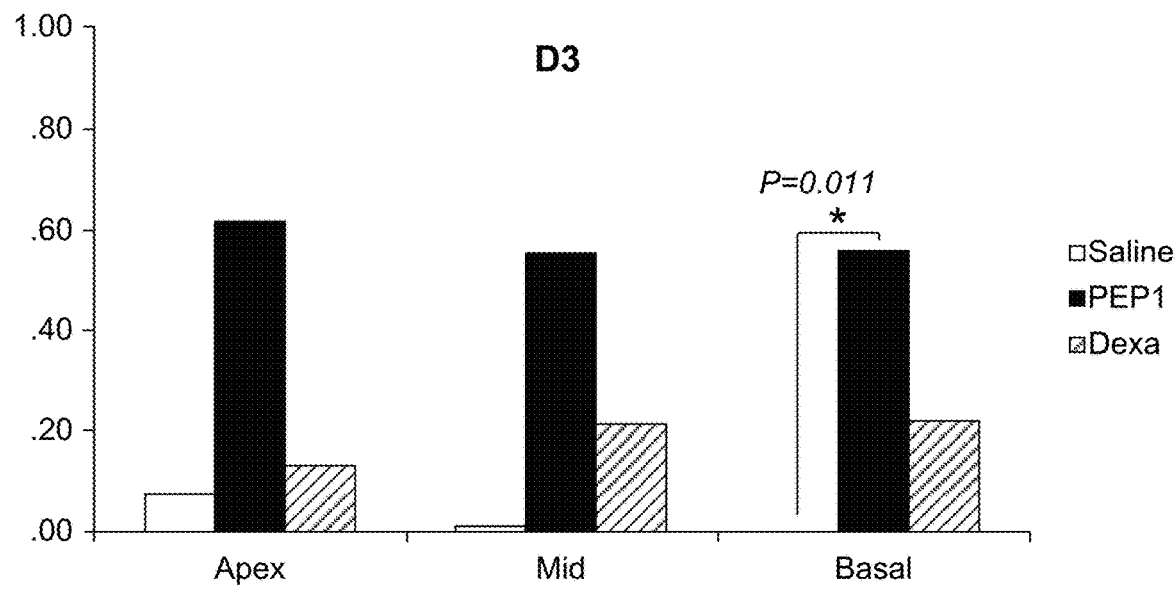

FIG. 17 is a graph showing quantitative analysis results of a ratio of normal hair cells of basal, mid, and apex of the cochlea after performing biopsy on ototoxic animal models including PEP1-administered Experimental Group 3, dexamethasone-administered Experimental Group 4, and saline solution-administered Control 2, respectively, according to the schedule of Experiment D3.

Figure 18:
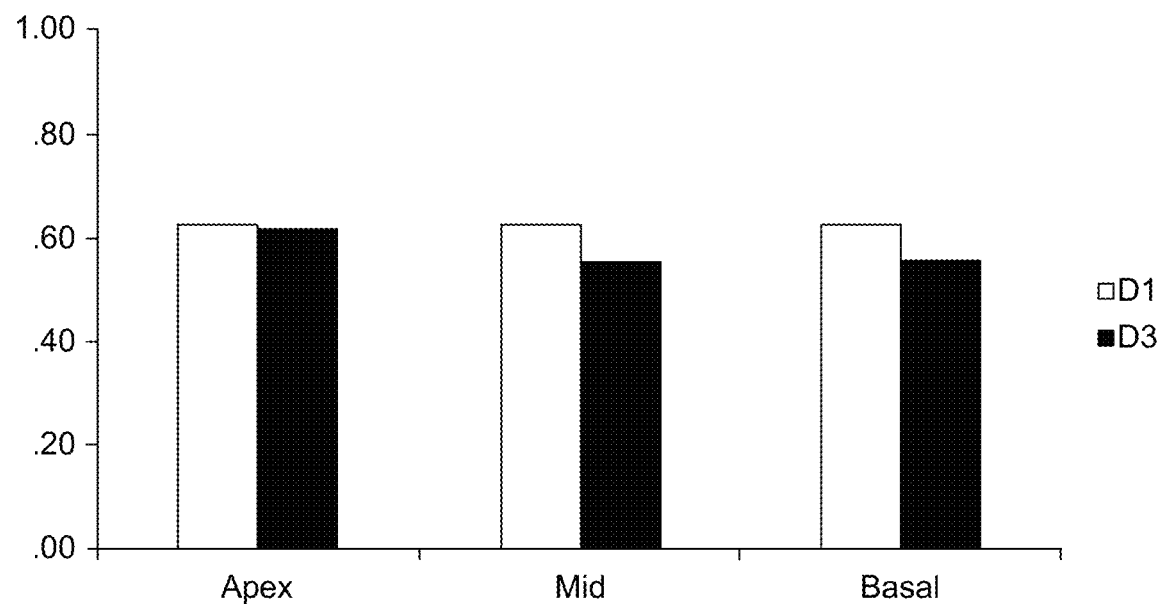

FIG. 18 is a graph showing quantitative and comparative analysis results of a ratio of normal hair cells of basal, mid, and apex of the cochlea after performing biopsy on PEP1-administered Experimental Groups 1 and 3 as ototoxic animal models according to the schedules of Experiments D1 and D3, respectively.

DETAILED DESCRIPTION OF THE INVENTION

Best Mode

Although the present invention allows for various changes and numerous embodiments, particular embodiments of the present invention will now be described in more detail. However, it is not intended to limit the present invention to particular modes of practice, and it should be construed as including all changes, equivalents, and substitutes within the spirit and scope of the present invention. In the description of the present invention, certain detailed explanations of related art are omitted when it is deemed that they may unnecessarily obscure the essence of the invention.

A telomere is a genetic material that is repeatedly present at an end of a chromosome and is known to prevent damage to the corresponding chromosome or binding thereof to other chromosomes. When a cell divides, the length of the telomere gradually decreases, and, when cell division occurs a certain number of times or more, the telomere becomes very short, and the cell stops dividing and dies. In contrast, it is known that, when telomeres are lengthened, lifespan of the cells is extended. For example, it is known that, in cancer cells, telomerase is secreted to prevent the telomeres from being shortened, and thus the cancer cells do not die and can continuously propagate. The inventors of the present invention verified that a peptide derived from telomerase is effective in suppressing angiogenesis, thus completing the present invention.

A peptide disclosed in the present specification may include peptides having 80% or more sequence homology, 85% or more sequence homology, 90% or more sequence homology, 95% or more sequence homology, 96% or more sequence homology, 97% or more sequence homology, 98% or more sequence homology, and 99% or more sequence homology. In addition, the peptide disclosed in the present specification may include a peptide having a sequence of SEQ ID NO: 1 or fragments thereof, and peptides in which one or more amino acids, two or more amino acids, three or more amino acids, four or more amino acids, five or more amino acids, six or more amino acids, or seven or more amino acids are modified.

In one embodiment of the present invention, an amino acid modification refers to a change in physical and chemical properties of peptides. For example, amino acid changes, to improve thermal stability of peptides, change substrate specificity, change the optimum pH, and the like, may be performed.

In addition, the peptide having a sequence of SEQ ID NO: 1, the fragment thereof, or the peptide having 80% or more sequence homology to the above-described peptide sequence, according to one embodiment of the present invention has low intracellular toxicity and high in vivo stability. In the present invention, the peptide with SEQ ID NO: 1 is a telomerase-derived peptide and a peptide consisting of 16 amino acids as follows.

The peptide shown in SEQ ID NO: 1 is as shown in Table 1 below. In Table 1 below, "name" is used to distinguish peptides from each other. In one embodiment of the present invention, the peptide shown in SEQ ID NO: 1 refers to a whole peptide of human telomerase. According to another embodiment of the present invention, the peptide having a sequence of SEQ ID NO: 1, the fragment thereof, or the peptide having 80% or more sequence homology to the above-described peptide sequence includes a synthetic peptide obtained by selecting and synthesizing peptides at corresponding positions from among peptides included in telomerase. SEQ ID NO: 2 denotes an amino acid sequence of whole telomerase.

TABLE 1

| SEQ ID NO. | Name | Position on telomerase | Sequence | Length |
| --- | --- | --- | --- | --- |
| 1 | pep1 | [611-626] | EARPALLTSRLRFIPK | 16 aa |
| 2 | | [1-1132] | MPRAPRCRAVRSLLRSHYREVLPLATFV RRLGPQGWRLVQRGDPAAFRALVAQCL VCVPWDARPPPAAPSFRQVSCLKELVAR VLQRLCERGAKNVLAFGFALLDGARGGP PEAFTTSVRSYLPNTVTDALRGSGAWGL LLRRVGDDVLVHLLARCALFVLVAPSCA YQVCGPPLYQLGAATQARPPPHASGPRR RLGCERAWNHSVREAGVPLGLPAPGAR RRGGSASRSLPLPKRPRR GAAPEPERTPVGQGSWAHPGRTRGPSDR GFCVVSPARPAEEATSLEGALSGTRHSHP SVGRQHHAGPPSTSRPPRPWDTPCPPVY AETKHFLYSSGDKEQLRPSFLLSSLRPSLT | 1132 aa |

TABLE 1-continued

| SEQ ID NO. | Name | Position on telomerase | Sequence | Length |
|---|---|---|---|---|
| | | | GARRLVETIFLGSRPWMPGTPRRLPRLPQ | |
| | | | RYWQMRPLFLELLGNHAQCPYGVLLKT | |
| | | | HCPLRAAVTPAAGVCAREKPQGSVAAPE | |
| | | | EEDTDPRRLVQLLRQHSSPWQVYGFVRA | |
| | | | CLRRLVPPGLWGSRHNERRFLRNTKKFIS | |
| | | | LGKHAKLSLQELTWKMSVRDCAWLRRS | |
| | | | PGVGCVPAAEHRLREEILAKFLHWLMSV | |
| | | | YVVELLRSFFYVTETTFQKNRLFFYRKSV | |
| | | | WSKLQSIGIRQHLKRVQLRELSEAEVRQ | |
| | | | HREARPALLTSRLRFIPKPDGLRPIVNMD | |
| | | | YVVGARTFRREKRAERLTSRVKALFSVL | |
| | | | NYERARRPGLLGASVLGLDDIHRAWRTF | |
| | | | VLRVRAQDPPPELYFVKVDVTGAYDTIP | |
| | | | QDRLTEVIASIIKPQNTYCVRRYAVVQKA | |
| | | | AHGHVRKAFKSHVSTLTDLQPYMRQFV | |
| | | | AHLQETSPLRDAVVIEQSSSLNEASSGLF | |
| | | | DVFLRFMCHHAVRIRGKSYVQCQGIPQG | |
| | | | SILSTLLCSLCYGDMENKLFAGIRRDGLL | |
| | | | LRLVDDFLLVTPHLTHAKTFLRTLVRGV | |
| | | | PEYGCVVNLRKTVVNFPVEDEALGGTAF | |
| | | | VQMPAHGLFPWCGLLLDTRTLEVQSDYS | |
| | | | SYARTSIRASLTFNRGFKAGRNMRRKLF | |
| | | | GVLRLKCHSLFLDLQVNSLQTVCTNIYKI | |
| | | | LLLQAYRFHACVLQLPFHQQVWKNPTFF | |
| | | | LRVISDTASLCYSILKAKNAGMSLGAKG | |
| | | | AAGPLPSEAVQWLCHQAFLLKLTRHRVT | |
| | | | YVPLLGSLRTAQTQLSRKLPGT | |
| | | | TLTALEAAANPALPSDFKTILD | |

Kanamycin used in experiments of the present invention is an aminoglycoside-based antibiotic. Only 3% of a dose of an aminoglycoside is absorbed into the stomach, and thus the aminoglycoside is administered via injection, and the administered drug is mostly excreted via urine through glomerular filtration. In the case of renal failure, a secretion amount of aminoglycoside decreases and the drug is excessively accumulated in perilymph of the inner ear, and thus ototoxicity, like nephrotoxicity, is likely to occur. In particular, kanamycin is a drug with toxicity to the cochlea which destructs outer hair cells at a basal turn of the cochlea at an early stage together with neomycin, amikacin, sisomycin, and livodomycin, and, as kanamycin continues to be administered, a destruction site thereof expands to an apical turn.

Furosemide used in experiments of the present invention is a diuretic used to treat hypertension or edema by removing moisture and salts unnecessarily accumulated in the body. It has been reported that, in a case in which a high dose of furosemide is used or furosemide is used in a patient with hypoproteinemia or the like, or when furosemide is used in combination with other ototoxic drugs, tinnitus, hearing damage, or hearing loss occurs.

Dexamethasone used in experiments of the present invention is a synthetic corticosteroid drug and used as an anti-inflammation agent or an immunosuppressant. Dexamethasone is used for the treatment of various types of inflammatory diseases and as an immunosuppressant therefor, and is effective with respect to tinnitus, hearing loss, vestibular abnormalities. However, it has been reported that, when an excess amount of dexamethasone is administered, the drug excessively inhibits immune action, and causes severe side effects in patients with mycotic infection diseases in the eyes or the ears.

The auditory brainstem response (ABR) test used in experiments of the present invention to identify hearing loss is an accurate hearing test in which brainwaves from the nerve center of the brain are averaged, which can be obtained by auditory stimulation, and a threshold value of hearing is determined. As the threshold value increases, this indicates hearing loss is more severe.

According to one embodiment of the present invention, there is provided a pharmaceutical composition including, as an active ingredient, a peptide having an amino acid sequence of SEQ ID NO: 1, a peptide having 80% or more sequence homology to the amino acid sequence, or a fragment thereof that has an effect of treating hearing loss.

In the composition for the treatment of hearing loss, according to one embodiment of the present invention, the content of the peptide having an amino acid sequence of SEQ ID NO: 1, the peptide having 80% or more sequence homology to the amino acid sequence, or the fragment thereof may range from 0.01 g/L to 1 kg/L, in particular, 0.1 g/L to 100 g/L, more particularly, from 1 g/L to 10 g/L. However, when a difference in effects according to dose is shown, the content thereof may be appropriately adjusted. When the content of the above-listed peptide is within the above-described ranges or less, not only it is sufficient to exhibit desired effects of the present invention, but also both stability and safety of the composition may be satisfied, and it may be appropriate in terms of effects relative to costs.

The composition according to one embodiment of the present invention may be applied to all animals including humans, dogs, chickens, pigs, cows, sheep, guinea pigs, or monkeys.

As the composition according to one embodiment of the present invention, a pharmaceutical composition including a peptide having an amino acid sequence of SEQ ID NO: 1, a peptide having 80% or more sequence homology to the amino acid sequence, or a fragment thereof is provided. The pharmaceutical composition according to one embodiment of the present invention may be administered orally, intrarectally, percutaneously, intravenously, intramuscularly, intraperitoneally, intramedullary, intradurally, subcutaneously, or the like.

A preparation for oral administration may be a tablet, a pill, a soft or hard capsule, a granule, powder, a liquid preparation, or an emulsion, but the present invention is not limited thereto. A formation for parenteral administration may be an injection, a dripping agent, a lotion, an ointment, a gel, a cream, a suspension, an emulsion, a suppository, a patch, or a spraying agent, but the present invention is not limited thereto.

The pharmaceutical composition according to one embodiment of the present invention may include an additive such as a diluent, an excipient, a lubricant, a binder, a disintegrant, a buffer, a dispersant, a surfactant, a colorant, a flavoring, a sweetener, or the like according to need. The pharmaceutical composition according to one embodiment of the present invention may be prepared using a method commonly used in the art.

The active ingredient of the pharmaceutical composition according to one embodiment of the present invention may vary depending on ages of subjects to which the active ingredient is to be administered, gender, body weight, pathologic conditions and severity, administration route, or determination of prescribers. Determination of a suitable dose based on these factors may be within the range known by those of ordinary skill in the art, and a daily dose of the pharmaceutical composition may range, for example, from 10 ng/kg/day to 100 g/kg/day, in particular, from 0.1 µg/kg/day to 10 g/kg/day, more particularly, from 1 µg/kg/day to 1 g/kg/day, even more particularly, from 2 µg/kg/day to 100 mg/kg/day. When a difference in effects according to dose is shown, the daily dose may be appropriately adjusted. The pharmaceutical composition according to one embodiment of the present invention may be administered once to three times daily, but the present invention is not limited thereto.

As the composition according to one embodiment of the present invention, a food composition including, as an active ingredient, a peptide having an amino acid sequence of SEQ ID NO: 1, a peptide having 80% or more sequence homology to the amino acid sequence, or a fragment thereof is provided.

A preparation of the food composition according to one embodiment of the present invention is not particularly limited, and may be, for example, a tablet, a granule, powder, a liquid preparation, a solid preparation, or the like. Each preparation may be prepared by formulating ingredients commonly used in the art in addition to the active ingredient or appropriately selecting and mixing the ingredients by one of ordinary skill without undue difficulty according to the purpose of use. In addition, when used simultaneously with other raw materials, the ingredients may have a synergistic effect.

Terms used in the present specification are provided only to describe particular embodiments, and are not intended to limit the present invention. Terms that do not mention whether the noun is singular or plural are not intended to limit the number, but indicate that the mentioned noun exists in either a singular or plural form. The terms "including," "having," and "comprising" are interpreted as open terms (i.e., including, but not limited thereto).

Referring to a range of the values is an easy way to avoid individually mentioning each separate value within the range, and, unless otherwise stated herein, each separate value is incorporated in the present specification as if it is individually mentioned herein. The limit values of all the ranges are within the ranges and may be independently combined.

All the methods mentioned herein may be performed in a suitable order unless otherwise indicated or clearly contradicted by the context. The use of any one embodiment and all embodiments or exemplary languages (e.g., "such as") is intended to more fully describe the present invention and is not intended to limit the scope of the present invention unless it is within the claims. Any language in the specification should not be interpreted such that any unclaimed elements are essential to the practice of the present invention. Unless otherwise defined, technical and scientific terms used herein have the same meaning as commonly understood by one of ordinary skill in the art to which the invention pertains.

Exemplary embodiments of the present invention include the best mode known to inventors to implement the present invention. Variations of the exemplary embodiments may be obvious to those of ordinary skill in the art after reading the foregoing description. The inventors of the present invention expect that one of ordinary skill in the art appropriately uses such variations, and expect that the present invention is carried out in a manner different from that described herein. Thus, the present invention includes equivalents to and all modifications of the subject matter of the invention mentioned in the appended claims, as is permitted by the patent laws. In addition, all possible combinations of the aforementioned elements are included in the present invention within all possible variations when stated in a contrary manner or unless clearly contradicted by the context. Although the present invention has been described in detail with reference to exemplary embodiments thereof, it will be well understood by those of ordinary skill in the art that various changes in form and details can be made without departing from the spirit and scope of the invention defined by the following claims.

Hereinafter, configurations and effects of the present invention will be described in further detail with reference to examples and experimental examples. However, these examples and experimental examples are provided only for illustrative purposes to aid in understanding the present invention and are not intended to limit the spirt and the scope of the present invention.

MODE OF THE INVENTION

Example 1: Synthesis of Peptide

A peptide of SEQ ID NO: 1 (hereinafter, referred to as "PEP1") was prepared according to a generally known solid-phase peptide synthesis method. In particular, peptides were synthesized by Fmoc solid phase peptide synthesis (SPPS) using ASP48S (Peptron, Inc., Daej eon, Korea) by coupling amino acids one by one from the C-terminal. The first amino acid used at the C-terminus of each of the peptides, which was attached to a resin, is as follows:
$NH_2$-Lys(Boc)-2-chloro-trityl resin
$NH_2$-Ala-2-chloro-trityl resin
$NH_2$-Arg(Pbf)-2-chloro-trityl resin All amino acids used in the peptide synthesis were protected by Trt, Boc, t-butylester (t-Bu), 2,2,4,6,7-pentamethyl dihydro-benzofuran-5-sulfonyl (Pbf), or the like, whereas the N-terminus was protected by Fmoc, and the residues were all removed in acid. For example, the amino acids were as follows: Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-mercaptoacetic acid.

2-(1H-benzotriazole-1-yl)-1,1,3,3-tetamethylaminium hexafluorophosphate (HBTU)/N-hydroxybenzotriazole (HOBt)]/4-methylmorpholine (NMM) was used as a coupling reagent. Fmoc was removed using 20% piperidine in DMF. Each synthesized peptide was detached from the resin and the protective groups of the residues were removed using a cleavage cocktail [trifluoroacetic acid (TFA)/triisopropylsilane (TIS)/ethanedithiol (EDT)/H$_2$O=92.5/2.5/2.5/2.5].

Each peptide was synthesized by repeating a process of reacting a corresponding amino acid with a solid support to which a starting amino acid with a protective group bound thereto was bound, followed by washing with a solvent, and then deprotecting. The synthesized peptide was detached from the resin and purified with high performance liquid chromatography (HPLC), and then it was identified by MS whether the peptide was synthesized or not, followed by lyophilization.

As a result of performing HPLC on the peptide used in the present embodiment, the purity of all the peptides was 95% or more.

A process of preparing the peptide PEP1 will now be described in detail as follows.

1) Coupling 8 equivalents of the protected amino acid and HBTU (8 equivalents)/HOBt (8 equivalents)/NMM (16 equivalents) as a coupling reagent were dissolved in DMF and added to NH$_2$-Lys(Boc)-2-chloro-trityl resin, and then a reaction was allowed to occur therebetween at room temperature for 2 hours, and the reaction product was washed with DMF, MeOH, and DIVIF in this order.

2) Fmoc deprotection

20% piperidine in DMF was added to the resulting product, a reaction was allowed to occur therebetween at room temperature twice for 5 minutes, followed by washing with DMF, MeOH, and DMF in this order.

3) Reactions of 1 and 2 were repeated to thereby prepare NH$_2$-E(OtBu)-A-R(Pbf)-P-A-L-L-T(tBu)-S(tBu)-R(Pbf)L-R(Pbf)-F-I-P-K(Boc)-2-chloro-trityl resin (SEQ ID NO:3) as a peptide backbone.

4) Cleavage: The synthesis-completed peptide resin was treated with a cleavage cocktail to separate the peptide from the resin.

5) Cooling diethyl ether was added to the obtained mixture, and then the resulting mixture was centrifuged to precipitate the obtained peptide.

6) After purification with Prep-HPLC, the molecular weight was identified by LC/MS, and the resultant was frozen to be prepared as powder.

Example 2: Confirmation of Effect of PEP1 on Hearing Loss Due to Ototoxic Drug

Preparation of Experimental Animals and Injections

For an experiment, C57/BL6 mice (4-week-old to 6-week-old, body weight of 15 g to 25 g, male) were prepared. As an ototoxic drug, kanamycin in the form of kanamycin sulfate was dissolved in saline solution at a concentration of 40 mg/ml was prepared as a preparation for 800 mg/kg injection administration, and the peptide synthesized according to Example 1, i.e., PEP1, was prepared as a preparation for injection administration by dissolving 100 mg of PEP1 in 10 ml PBS.

Classification of Experimental Groups Administered Ototoxic Drug and Ototoxic Drug and PEP1

Kanamycin, which is an ototoxic drug, and the peptide according to the present invention, i.e., PEP1, were administered to the prepared experimental animals after dividing the animals into experimental groups.

Experimental Group 1: kanamycin 800 mg/kg S.C (subcutaneous injection)+saline 0.1 ml/10 g mice I.P. (intraperitoneal injection)

Experimental Group 2: kanamycin 800 mg/kg S.C.+PEP1 10 mg/kg I.P.

A dose for each experimental group was injected twice daily for 14 days.

Biopsy

Three weeks after the experiment started, the mice were euthanized, and then blood samples were collected therefrom, the mice were subjected to perfusion fixation with 4% paraformaldehyde (pH 7.4) diluted with 0.1 M phosphate buffered saline, and an organ (the temporal bone) was extracted from each mouse.

To observe an overall structure of the cochlea and the vestibule, the mice were fixed in 4% paraformaldehyde (pH 7.4) at 4° C. for 24 hours, and then maintained in 0.135M EDTA for three days to allow decalcification to occur. Tissue blocks were made using an optical cutting temperature compound (OCT compound) as an embedding agent for freezing and then stored at −80° C. and made in slide forms, followed by H&E staining.

To quantitatively analyze the temporal bone on the left side, a whole mount of the cochlea was prepared. The cochlear bony labyrinth was cautiously separated from the cochlear membranous labyrinth using a micro-instrument and a microscope and the apical turn and the basal turn were separated. Each of a side wall with the stria vascularis and a basilar membrane region of the cochlea was separated and then fixed with 4% paraformaldehyde. The resultants were reacted with 0.3% Triton-X for 1 hour, and then Alexa 488 phalloidin and 1% bovine serum albumin (BSA) were prepared. Alexa 488 phalloidin dissolved in methanol and 1% BSA were mixed in a ratio of 1:100. The resulting mixture was dispensed into the tissue samples and a reaction was allowed to occur in a shaker for 1 hour, followed by washing and fixing with 4% paraformaldehyde. A droplet of a vector was dropped onto a slide glass and the separated tissue was mounted thereon, and then fixed with a cover glass. All cochlear tissue samples and renal tissue samples of controls and experimental groups were observed using a confocal microscope under the same intensity conditions.

Perform Auditory Brainstem Response (ABR) Test

An ABR test was performed before injection, 1 week after injection, 2 weeks after injection, and 3 weeks after injection. Hearing was evaluated using negative stimuli of 4 kHz, 8 kHz, 16 kHz, and 32 kHz and, in ABR, the smallest stimulus intensity showing waveform #5 was determined as a threshold. Prior to drug administration, baseline hearing was measured in all the groups, and measurement was performed after anesthetizing each group via intraperitoneal injection of isoflorane.

Statistical Processing

Threshold values according to each frequency obtained as a result of the ABR test were added up, and statistical significance of the hearing threshold of each of Experimental Groups 1 and 2 was confirmed using a Mann-Whitney test.

The number of undamaged hair cells according to cochlear sites of the basal turn, the middle turn, and the apical turn was added up, and statistical significance of the number of hair cells of each of Experimental Groups 1 and 2 was confirmed using a Mann-Whitney test.

Analysis of Biopsy Results

Figure 1:
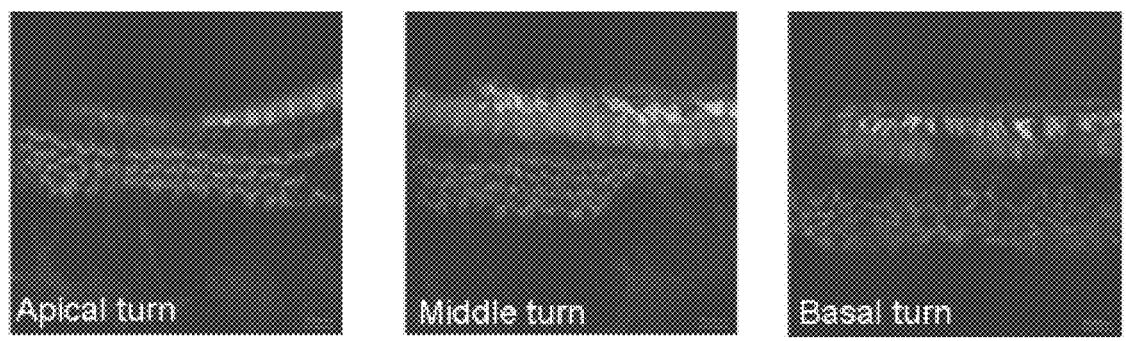
FIG. 1 illustrates images of hair cells at an apical turn, a middle turn, and a basal turn of cochlear tissue of an ototoxic animal model administered kanamycin.
Figure 2:
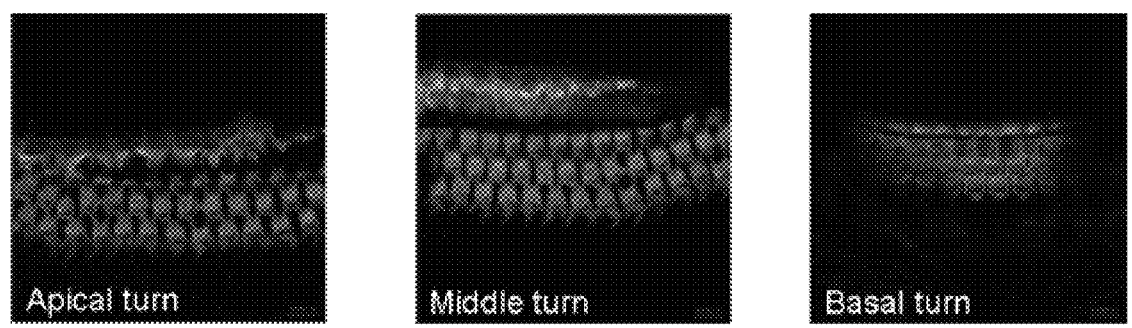
FIG. 2 illustrates image of hair cells at an apical turn, a middle turn, and a basal turn of cochlear tissue of animal models administered kanamycin and PEP1 in combination.

As a result of observation of hair cells at the basal turn, the middle turn, and the apical turn of the cochlea through biopsy, overall damage to hair cells in all the sites was observed in Experimental Group 1 (see FIG. 1). In contrast, no damage to hair cells was observed in all the sites in Experimental Group 2 (see FIG. 2).

Figure 3:
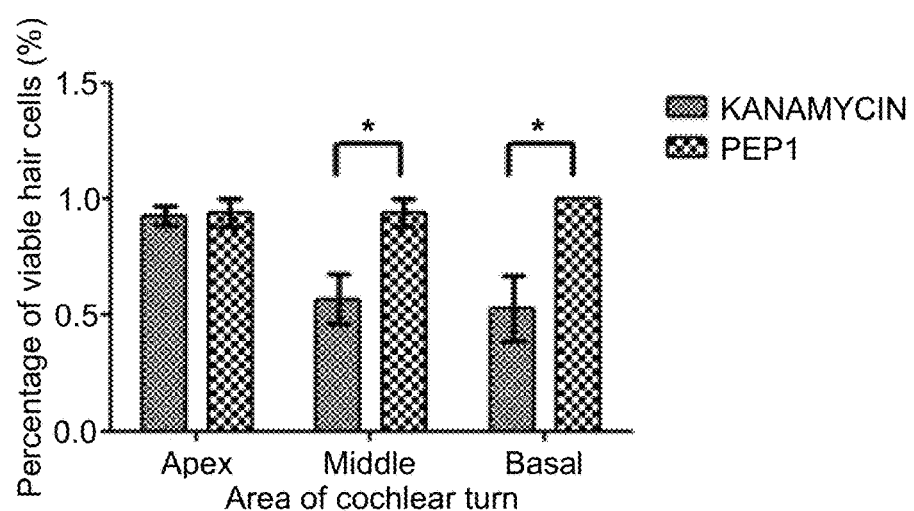
FIG. 3 is a graph showing results of comparison between the counted number of hair cells of a kanamycin-administered group and the counted number of hair cells of a group administered kanamycin and PEP1 in combination, at an apical turn, a middle turn, and a basal turn, wherein the counted number is expressed as percentage.

In addition, as a result of counting the number of hair cells in biopsy, a statistically significant (* denotes p<0.001) greater number of hair cells was confirmed at the middle turn and the basal turn of the cochlea in Experimental Group 2 than in Experimental Group 1 (see FIG. 3).

Figure 4:
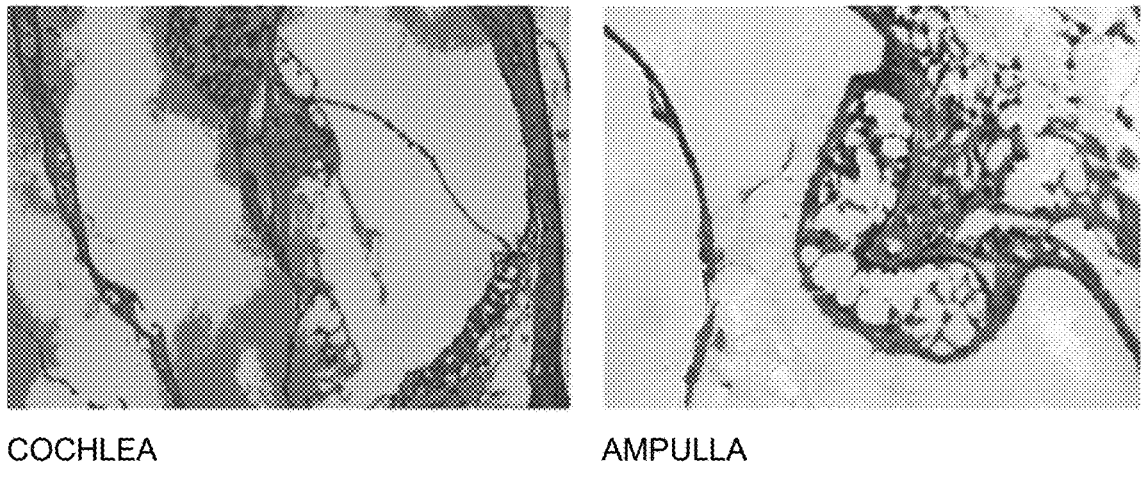
FIG. 4 illustrates hematoxylin & eosin (H&E) staining images of frozen cochlear and ampullar tissue sections of an ototoxic animal model administered kanamycin.
Figure 5:
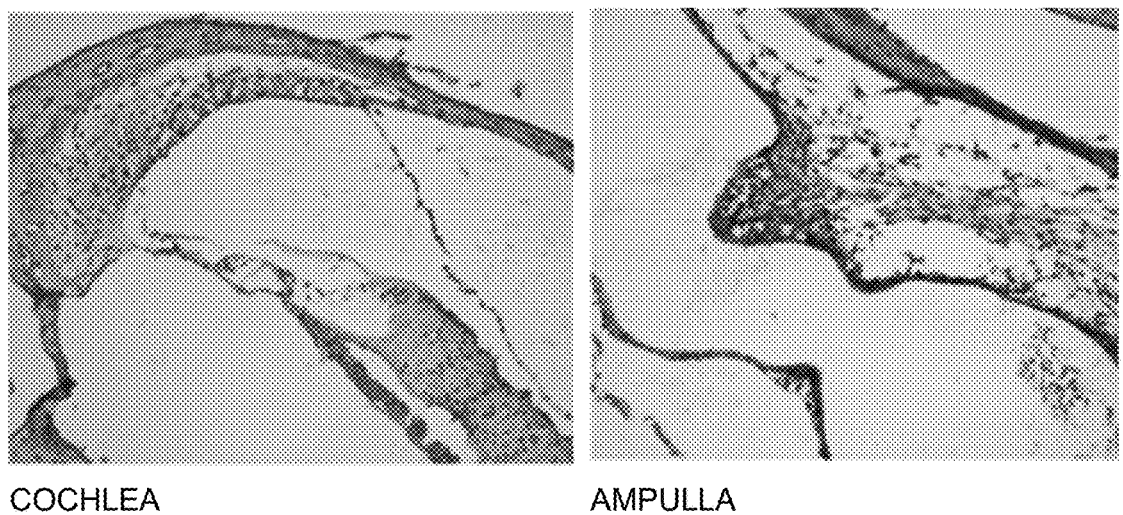
FIG. 5 illustrates H&E staining images of frozen cochlear and ampullar tissue sections of an animal group administered kanamycin and PEP1 in combination.

In addition, as a result of H&E staining results of frozen cochlear and ampullar tissue sections obtained in biopsy, in Experimental Group 1, loss of cochlear hair cells was observed, normal ampullar sensory epithelium disappeared, and vacuolization considerably occurred (see FIG. 4). In contrast, it was observed in Experimental Group 2 that normal cochlear hair cells and normal ampullar sensory epithelium were conserved (see FIG. 5).

Analysis of ABR Test Results

Figure 6:
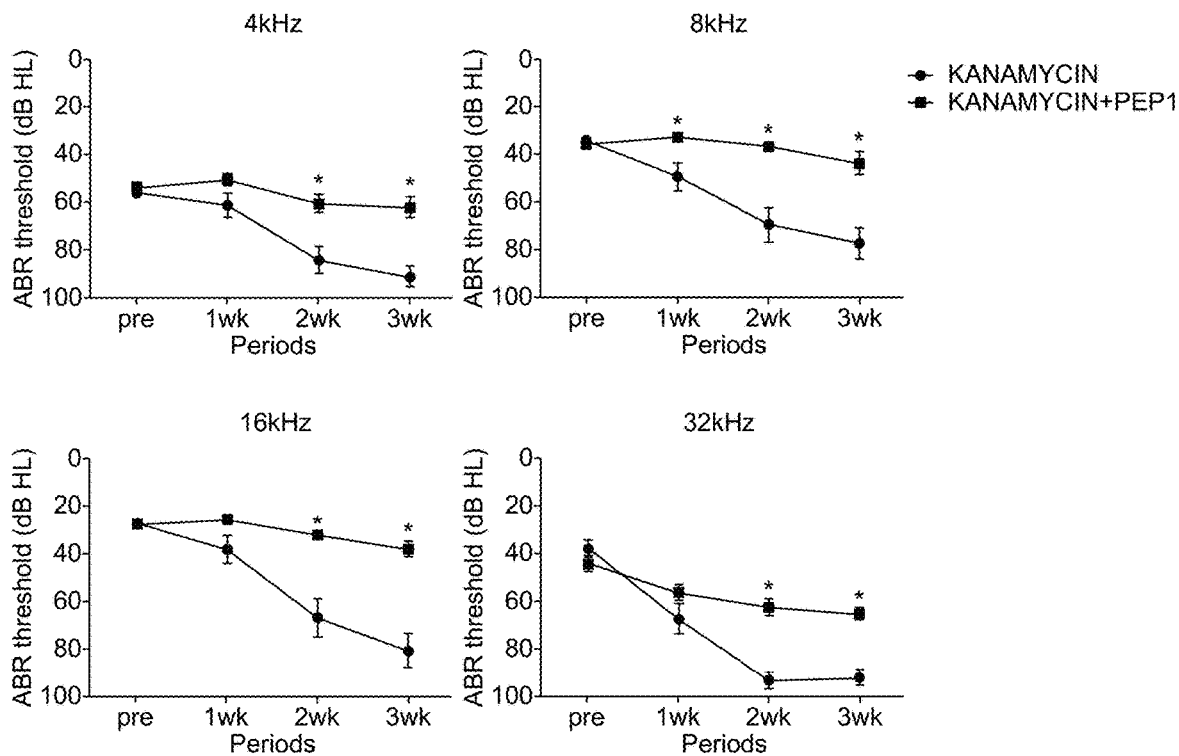
FIG. 6 illustrates graphs showing a degree of hearing loss of each of a kanamycin-administered group and a group administered kanamycin and concentration-based PEP1 through an auditory brainstem response (ABR) test according to frequency bands.

As a result of observation of changes in hearing over time after drug administration through an ABR test, the threshold value increased over time in Experimental Group 1, while a change in the threshold value was insignificant over time in Experimental Group 2 (see FIG. 6). A difference in the results of the two groups was statistically significant (* denotes p<0.001).

Example 3: Confirmation of the Presence or Absence of Ototoxic Hearing Loss According to Administration of PEP1

Preparation of Experimental Animal and Injection for Each Experimental Group

For an experiment, C57/BL6 mice (4-week-old to 6-week-old, body weight of 15 g to 25 g, male) were prepared. To administer PEP1 according to concentration, PEP1 synthesized using the method according to Example 1 and a saline solution as a control were prepared. PEP1 was prepared by setting a baseline concentration of 10 mg/ml as 1 solution unit. The control and groups administered PEP1 according to concentration were prepared as follows:

Experimental Group 3: Control, administered saline solution (physiological saline 10 ml)
Experimental Group 4: administered 0.1 mg/kg of PEP1 (1 solution unit 1 ml+PBS 9 ml)
Experimental Group 5: administered 1 mg/kg of PEP1 (10 solution units 1 ml+PBS 9 ml)
Experimental Group 6: administered 10 mg/kg of PEP1 (100 solution units 1 ml+PBS 9 ml)
Experimental Group 7: administered 100 mg/kg of PEP1 (PEP1 100 mg+PBS 10 ml)

A dose of 0.1 ml/10 g (weight of mouse) per one time was intraperitoneally injected at the concentration of each experimental group. Injection was performed twice (9 am and 5 pm) daily for 7 days.

Biopsy

Two weeks after the start of an experiment, animal groups were euthanized and samples for biopsy were collected using the method as in Example 2.

Analysis of Biopsy Results

Figure 7:
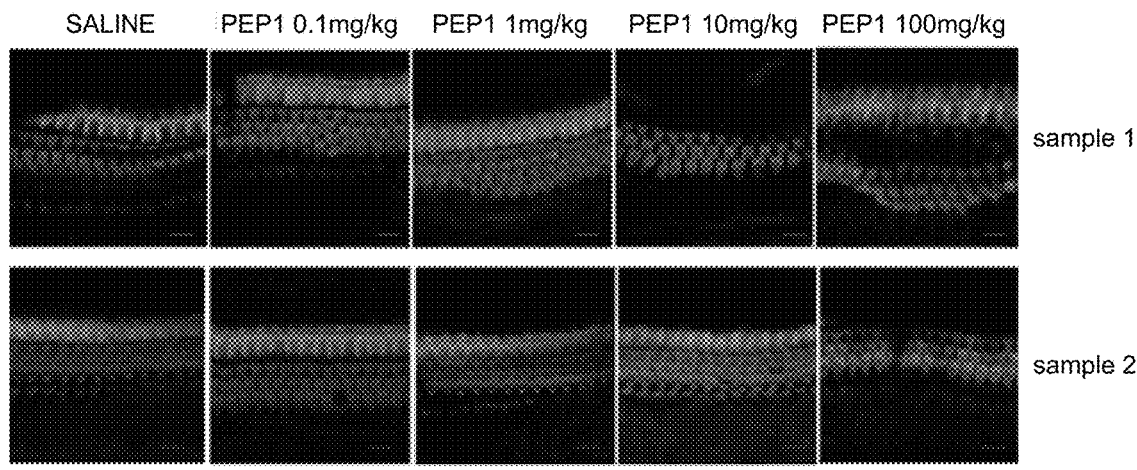
FIG. 7 illustrates images of hair cells of cochlear tissue samples of a control without PEP1 and groups treated with PEP1 according to concentration twice daily for 2 weeks.

As a result of observation of hair cells at the basal turn, the middle turn, and the apical turn of the cochlea through biopsy, no damage to hair cells of the cochlea was observed in all the experimental groups (see FIG. 7).

Figure 8:
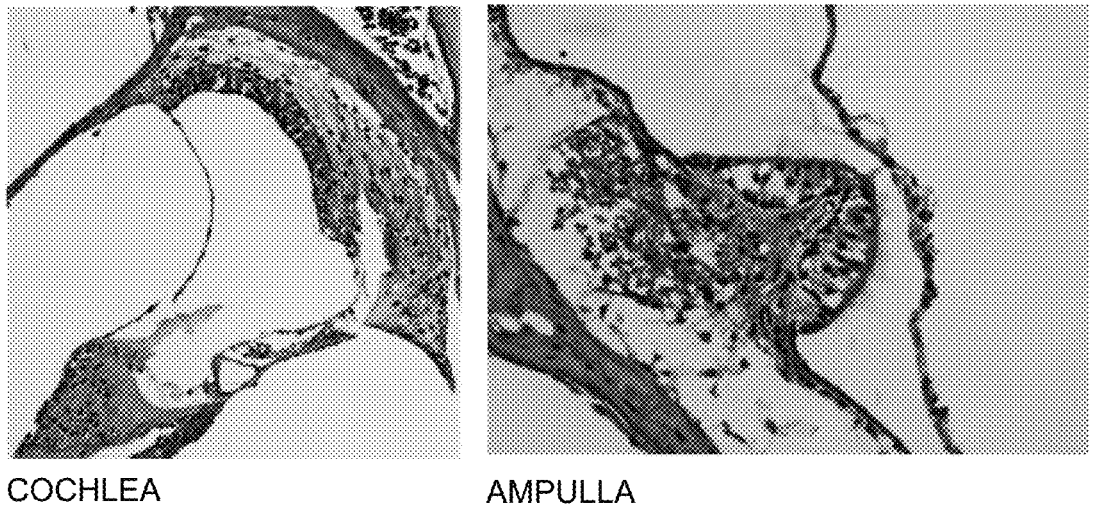
FIG. 8 illustrates H&E staining images of frozen cochlear and ampullar tissue sections of a control without PEP1.
Figure 9:
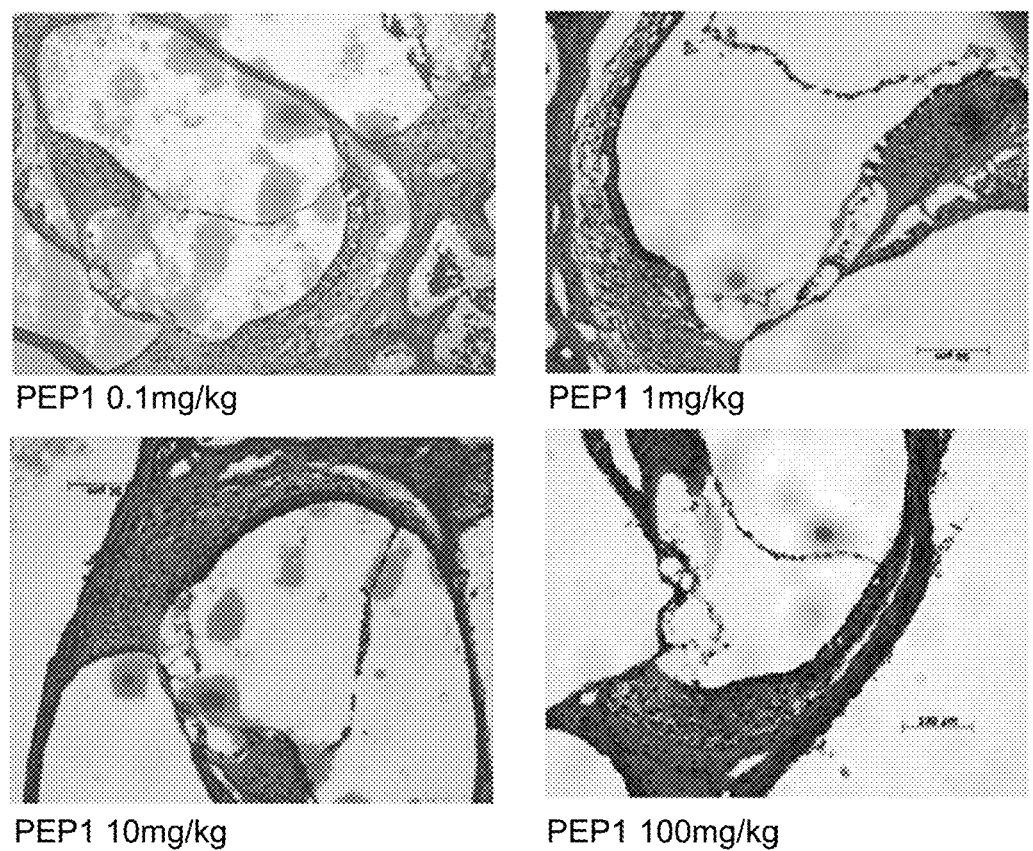
FIG. 9 illustrates H&E staining images of frozen cochlear and ampullar tissue sections of each experimental group administered PEP1 according to concentration.

In addition, as a result of observation of H&E stained cochlear and ampullar tissue obtained as frozen sections in biopsy, in Experimental Group 3 as a control, both cochlear hair cells and ampullar hair cells showed normal findings (see FIG. 8). As a result of observation of cochlear tissue sections of Experimental Groups 4 to 7 administered PEP1 according to concentration, no damage to the structure of the cochlea was observed (see FIG. 9).

Example 4: Confirmation of Effect of PEP1 on Hearing Loss Due to Two Types of Ototoxic Drugs and Comparison Thereof with Existing Drugs Preparation of Experimental Animal Model For an experiment, an ototoxic animal model was prepared by intraperitoneally administering 1000 mg/kg of kanamycin to C57/BL6 mice (5-week-old, body weight of 15 g to 25 g, female) and injecting 100 mg/kg of furosemide thereinto within 30 minutes.

Figure 10:
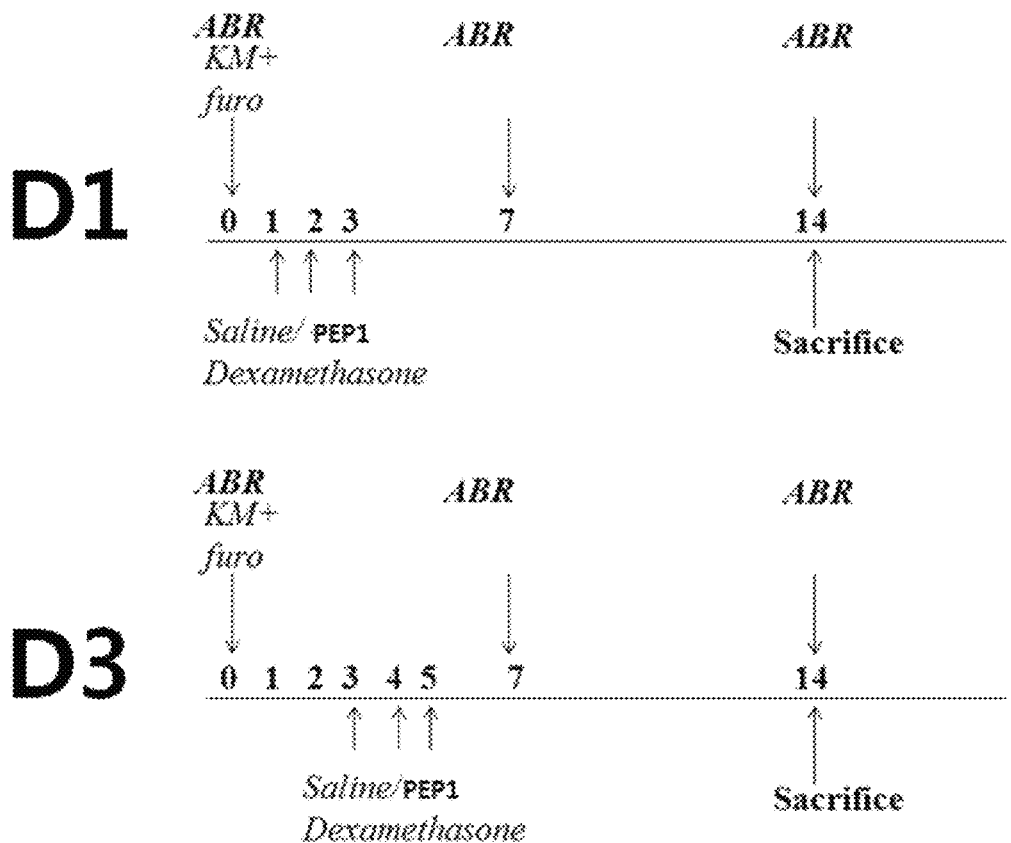
FIG. 10 is a protocol graph showing drug administration and ABR test schedules of an experiment performed at schedules D1 and D3 using an ototoxic animal model administered kanamycin, which is an ototoxic drug, and furosemide.

Classification and Preparation of Experimental Groups Administered Experimental Target Materials and Repeated Experiment 24 ototoxic animal models were classified into experimental groups and a control as follows and an experiment was carried out. The experimental name was indicated as D1 (See FIG. 10).

Experimental Group 1: 8 ototoxic animal models administered 10 mg/kg of PEP1 via subcutaneous injection on day 1, day 2, and day 3, respectively, after administration of kanamycin and furosemide
Experimental Group 2: 8 ototoxic animal models administered 15 mg/kg of dexamethasone via subcutaneous administration on day 1, day 2, and day 3, respectively after administration of kanamycin and furosemide
Control 1: 8 ototoxic animal models administered saline solution on day 1, day 2, and day 3, respectively after administration of kanamycin and furosemide In addition, to evaluate experimental results (i.e., a difference in effects according to administration time of an experimental substance) after administering an ototoxic drug to ototoxic animal models and taking more time for the ototoxicity to progress, 24 ototoxic animal models were classified into experimental groups and a control and an experiment was carried out. The experimental name was indicated as D3 (see FIG. 10).

Experimental Group 3: 8 ototoxic animal models administered 10 mg/kg of PEP1 via subcutaneous injection on day 3, day 4, and day 5, respectively after administration of kanamycin and furosemide
Experimental Group 4: 8 ototoxic animal models administered 15 mg/kg of dexamethasone via subcutaneous administration on day 3, day 4, and day 5, respectively after administration of kanamycin and furosemide
Control 2: 8 ototoxic animal models administered saline solution on day 3, day 4, and day 5, respectively after administration of kanamycin and furosemide Perform ABR Test An ABR test was performed prior to administration of kanamycin and furosemide (day 0), on day 7 after the administration, and on day 14 after the administration (The test was performed in the same manner for both Experiments D1 and D3). Hearing was evaluated using negative stimuli of 8 kHz, 16 kHz, and 32 kHz, and, in ABR, the smallest stimulus intensity showing waveform #5 was determined as a threshold. Prior to drug administration, baseline hearing was measured in all the groups, and measurement was performed after anesthetizing each group via intraperitoneal injection of isoflorane.

Biopsy

On day 14 after administration of kanamycin and furosemide, mice on which the ABR test was completed were euthanized, and then otic capsules were extracted therefrom and a degree of damage to hair cells was observed using a confocal scanning microscope.

Statistical Processing

Hearing threshold values measured in the ABR test and values of hair cells of each group measured in biopsy were statistically processed and significance thereof was confirmed. In this case, an ANOVA test was used.

Analysis of ABR Test Results

In experiment D1, as a result of observation of frequency-based hearing changes according to administered drugs, PEP1-administered Experimental Group 1 showed a smaller hearing threshold value measured on day 14 after administration of kanamycin and furosemide than that of saline solution-administered Control 2. In particular, a statistically significant difference was shown at 32 kHz (p=0.008, see FIG. 11).

In experiment D3, as a result of observation of frequency-based hearing changes according to administered drugs, PEP1-administered Experimental Group 3 showed a smaller hearing threshold value measured on day 14 after administration of kanamycin and furosemide than that of saline solution-administered Control 2 and dexamethasone-administered Experimental Group 4. In particular, statistically significant differences were shown at 8 kHz and 16 kHz (p=0.014, see FIG. 12).

As a result of observation of frequency-based hearing changes according to administration time of PEP1 by comparing experiment D1 with experiment D3, no significant difference in hearing threshold values measured prior to administration of kanamycin and furosemide, on day 7 after the administration, and on day 14 after the administration was shown (see FIG. 13).

Analysis of Biopsy Results

In Experiment D1, as a result of observation of the viability of hair cells at basal, mid, and apex of the cochlea through biopsy performed on day 14 after administration of kanamycin and furosemide, overall damage to hair cells at basal, mid, and apex of the cochlea was observed in saline solution-administered Control 1, and normal hair cells were observed in PEP1-administered Experimental Group 1 and dexamethasone-administered Experimental Group 2 (see FIG. 14).

In Experiment D3, as a result of observation of the viability of hair cells at basal, mid, and apex of the cochlea through biopsy performed on day 14 after administration of kanamycin and furosemide, overall damage to hair cells at basal, mid, and apex of the cochlea was observed in saline solution-administered Control 2, while normal hair cells were observed in PEP1-administered Experimental Group 3 and dexamethasone-administered Experimental Group 4 (see FIG. 15).

In Experiment D1, as a result of quantitative analysis of the viability of hair cells, the percentage of normal hair cells of PEP1-administered Experimental Group 1 at basal, mid, and apex of the cochlea was higher than that of saline solution-administered Control 1, and such a difference was statistically significant at mid and basal of the cochlea (p=0.006). In addition, the percentage of normal hair cells of PEP1-administered Experimental Group 1 was higher than that of dexamethasone-administered Experimental Group 2 (see FIG. 16).

In Experiment D3, as a result of quantitative analysis of the viability of hair cells, the percentage of normal hair cells of PEP1-administered Experimental Group 3 at basal, mid, and apex of the cochlea was higher than that of saline solution-administered Control 2, and such a difference was statistically significant at mid and basal of the cochlea (p=0.011). In addition, the percentage of normal hair cells of PEP1-administered Experimental Group 3 was higher than that of dexamethasone-administered Experimental Group 4 (see FIG. 17).

As a result of analysis of the percentage of normal hair cells according to administration time of PEP1 by comparing Experiment D1 with Experiment D3, the percentage of normal hair cells according to biopsy performed on day 14 after administration of kanamycin and furosemide did not show a significant difference (see FIG. 18).

In summary of the results of examples, from the experiment of Example 2, it can be confirmed that PEP1 prevents hearing loss and damage to hearing-related organs and tissue from a drug that causes hearing loss, and, from the experiment of Example 3, it can be confirmed that PEP1 prevents hearing loss and is not ototoxic to auditory organs according to administration thereof, thus being safe. In addition, from the experiment of Example 4, it can be confirmed that, when PEP1 is administered, the peptide functions to protect hearing from ototoxic hearing loss caused when two or more types of ototoxic materials are administered, and, in particular, a case, in which PEP1 is administered, exhibits a more excellent effect of preventing or alleviating hearing loss symptoms than that in a case in which dexamethasone known as an existing agent for alleviating hearing loss symptoms is administered.

In conclusion, it can be confirmed that a composition including PEP1 prevents or alleviate hearing loss, has no toxicity when administered, and may be used as a pharmaceutical composition for the treatment and prevention of hearing loss, which is more effective and safer than existing drugs, to treat and prevent hearing loss.

What is claimed is:

1. A method of treating hearing loss comprising:
administering an effective amount of a composition comprising the isolated peptide of SEQ ID NO: 1 to a subject in need thereof, wherein the hearing loss is caused by administration of an ototoxic drug or ototoxic drug treatment, and wherein the ototoxic drug is one or more drug selected from the group consisting of aminoglycoside-based antibiotics and diuretics.

2. The method of claim 1, wherein the aminoglycoside-based antibiotics comprise kanamycin, and the diuretics comprise furosemide.

3. The method of claim 1, wherein the composition is a pharmaceutical composition further comprising a pharmaceutically acceptable additive.

4. The method of claim 3, wherein the pharmaceutically acceptable additive is a diluent, an excipient, a lubricant, a binder, a disintegrant, a buffer, a dispersant, a surfactant, a colorant, a flavoring, or a sweetener.

5. The method of claim 1, wherein the pharmaceutical composition is administered orally, intrarectally, percutaneously, intravenously, intramuscularly, intraperitoneally, intramedullary, intradurally, or subcutaneously.

6. The method of claim 1, wherein the pharmaceutical composition is a tablet, a pill, a soft or hard capsule, a granule, powder, a liquid preparation, or an emulsion.

7. The method of claim 1, wherein the pharmaceutical composition is an injection, a dripping agent, a lotion, an ointment, a gel, a cream, a suspension, an emulsion, a suppository, a patch, or a spraying agent.

8. The method of claim 1, wherein the isolated peptide of SEQ ID NO: 1 is administered at a dose of from 10 ng/kg/day to 100 g/kg/day.

9. The method of claim 1, wherein the isolated peptide of SEQ ID NO: 1 is administered at a dose of from 2µg/kg/day to 100 mg/kg/day.

10. The method of claim 1, wherein pharmaceutical composition is administered once to three times daily.

11. A method of preventing hearing loss caused by administration of an ototoxic drug or ototoxic drug treatment comprising:
administering an effective amount of a composition comprising the isolated peptide of SEQ ID NO: 1 to a subject in need thereof, wherein the ototoxic drug is an aminoglycoside-based antibiotic.

12. The method of claim 11, wherein the aminoglycoside-based antibiotics comprise antibiotic comprises kanamycin.

13. The method of claim 11, wherein the composition is a pharmaceutical composition further comprising a pharmaceutically acceptable additive.

14. The method of claim 11, wherein the pharmaceutical composition is administered orally, intrarectally, percutaneously, intravenously, intramuscularly, intraperitoneally, intramedullary, intradurally, or subcutaneously.

15. The method of claim 11, wherein the pharmaceutical composition is a tablet, a pill, a soft or hard capsule, a granule, powder, a liquid preparation, or an emulsion.

16. The method of claim 11, wherein the pharmaceutical composition is an injection, a dripping agent, a lotion, an ointment, a gel, a cream, a suspension, an emulsion, a suppository, a patch, or a spraying agent.

17. The method of claim 11, wherein the isolated peptide of SEQ ID NO: 1 is administered after the ototoxic drug or ototoxic drug treatment.

* * * * *